(12) United States Patent
Canady et al.

(10) Patent No.: US 11,967,425 B2
(45) Date of Patent: Apr. 23, 2024

(54) SYSTEM AND METHOD FOR VOICE-CONTROL OF ELECTROSURGICAL SYSTEM

(71) Applicant: Jerome Canady Research Institute for Advanced Biological and Technological Sciences, Takoma Park, MD (US)

(72) Inventors: Jerome Canady, Lakeland, FL (US); Changhan Jun, Beltsville', MD (US); Taisen Zhuang, Rockville, MD (US)

(73) Assignee: Jerome Canady Research Institute, Takoma Park, MD (US)

( * ) Notice: Subject to any disclaimer, the term of this patent is extended or adjusted under 35 U.S.C. 154(b) by 307 days.

(21) Appl. No.: 17/471,828

(22) Filed: Sep. 10, 2021

(65) Prior Publication Data
US 2022/0076824 A1 Mar. 10, 2022

Related U.S. Application Data

(60) Provisional application No. 63/076,771, filed on Sep. 10, 2020.

(51) Int. Cl.
*G16H 40/67* (2018.01)
*A61B 18/12* (2006.01)
*A61B 34/30* (2016.01)

(52) U.S. Cl.
CPC ......... *G16H 40/67* (2018.01); *A61B 18/1206* (2013.01); *A61B 34/30* (2016.02); *A61B 2560/0493* (2013.01)

(58) Field of Classification Search
CPC ............... A61B 18/1206; A61B 34/30; A61B 2560/0493; G16H 40/67
See application file for complete search history.

(56) References Cited

U.S. PATENT DOCUMENTS

| 4,040,426 A | 8/1977 | Morrison |
| 4,429,694 A | 2/1984 | McGreevy |

(Continued)

FOREIGN PATENT DOCUMENTS

| CA | 2895975 A1 * | 6/2014 | ........... A61B 5/0035 |
| CA | 3112875 A1 * | 3/2020 | ......... A61B 17/3403 |

(Continued)

OTHER PUBLICATIONS

Zhang, Meng, Anand Raghunathan, and Niraj K. Jha. "Trustworthiness of medical devices and body area networks." Proceedings of the IEEE 102.8: 1174-1188. (Year: 2014).*

(Continued)

*Primary Examiner* — Daniel C Washburn
*Assistant Examiner* — Oluwadamilola M Ogunbiyi
(74) *Attorney, Agent, or Firm* — 24IP Law Group USA, PLLC; Timothy R DeWitt

(57) ABSTRACT

A system and method for voice control of operating room electrical equipment. The system comprises an electrosurgical generator a controller with a memory, a graphical user interface controlled by said controller, a power module, a field programmable gate array, and a voice recognition module connected to said field programmable gate array, a data storage connected to said controller in said electrosurgical generator; and electrical operating room equipment connected to said voice recognition module, wherein said electrical operating room equipment is configured to receive and decrypt encrypted commands from said voice recognition module. The electrical operating room equipment may said electrosurgical generator or a robotic surgical system or other electrical equipment in an operating room. The connection between said electrical operating room equipment and said voice recognition module may be wireless. The (Continued)

connection between said data storage and said controller in said electrosurgical system also may be wireless.

8 Claims, 6 Drawing Sheets

(56) References Cited

U.S. PATENT DOCUMENTS

| | | | |
|---|---|---|---|
| 4,781,175 A | 11/1988 | Bertrand et al. | |
| 5,207,675 A | 5/1993 | Canady | |
| 9,999,462 B2 | 6/2018 | Canady et al. | |
| 10,213,614 B2 | 2/2019 | Guron et al. | |
| 2011/0161111 A1* | 6/2011 | Dicks | A61B 5/0022 |
| | | | 705/3 |
| 2013/0296846 A1 | 11/2013 | Canady et al. | |
| 2014/0378892 A1 | 12/2014 | Guron et al. | |
| 2017/0000552 A1* | 1/2017 | Asher | A61B 18/1206 |
| 2021/0307841 A1* | 10/2021 | Buch | A61B 5/749 |
| 2022/0053283 A1* | 2/2022 | Beaurepaire | H04W 4/029 |
| 2022/0172721 A1* | 6/2022 | Tan | A61B 5/1114 |
| 2022/0239636 A1* | 7/2022 | Kreuzer | G06F 21/64 |
| 2023/0165644 A1* | 6/2023 | Deane | A61B 1/0016 |
| | | | 700/245 |

FOREIGN PATENT DOCUMENTS

| | | | | |
|---|---|---|---|---|
| KR | 20130104097 A | * | 9/2013 | G09B 9/00 |
| KR | 20150074313 A | * | 7/2015 | A61B 18/12 |
| WO | WO-2015017770 A1 | * | 2/2015 | A61M 1/1086 |
| WO | WO-2017160232 A1 | * | 9/2017 | G08B 21/043 |
| WO | WO-2018118415 A1 | * | 6/2018 | A61B 34/25 |
| WO | 2018191265 A1 | | 10/2018 | |
| WO | 2019199281 A1 | | 10/2019 | |

OTHER PUBLICATIONS

Zinchenko, Kateryna, Chien-Yu Wu, and Kai-Tai Song. "A study on speech recognition control for a surgical robot." IEEE Transactions on Industrial Informatics 13.2: 607-615. (Year: 2016).*

* cited by examiner

SYSTEM AND METHOD FOR VOICE-CONTROL OF ELECTROSURGICAL SYSTEM

CROSS-REFERENCE TO RELATED APPLICATIONS

The present application claims the benefit of the filing date of U.S. Provisional Patent Application Ser. No. 63/076,771 filed by the present inventors on Sep. 10, 2020.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to gas-enhanced electrosurgical systems, and more particularly, to a system and method for voice-control of a gas-enhanced electrosurgical system and other electronic operating room equipment.

Brief Description of the Related Art

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in U.S. Patent Application Publication No. 2013/0296846, which disclosed a system for simultaneously cutting and coagulating tissue. Another system, referred to as a "cold atmospheric plasma" system, is disclosed in U.S. Patent Application Publication No. 2014/0378892.

Several different systems and methods for performing Cold Atmospheric Plasma (CAP) treatment have been disclosed. For example, U.S. Pat. No. 10,213,614 discloses a two-electrode system for CAP treatment of cancer cells. Another exemplary Cold Atmospheric Plasma system is disclosed in U.S. Pat. No. 9,999,462. The disclosed system has two units, namely a Conversion Unit (CU) and a Cold Plasma Probe (CPP). The Conversion Unit is connected to high frequency electrosurgical generator (ESU) output and converts the ESU signal to a signal appropriate for performing cold atmospheric plasma procedures. The Cold Plasma Probe is connected to the Conversion Unit output. At the end of the Cold Plasma Probe cold plasma is produced and is thermally harmless to living tissue, i.e., it cannot cause burns to the tissue. This cold plasma, however, is deadly for cancer cells while leaving normal cells unaffected. The disclosed Cold Plasma Conversion Unit is unique in that it utilizes a high voltage transformer to up-convert the voltage (1.5-50 kV), down-convert the frequency (<300 kHz), and down-convert the power (<30 W) of the high-voltage output from an electrosurgical unit (U.S. Pat. No. 9,999,462).

Further, various systems and methods for controlling gas flow and an integrated gas-assisted electrosurgical generator having a graphical user interface is disclosed in WO2018/191265, entitled "Electrosurgical Gas Control Module" and WO2019199281, entitled "Gas Enhanced Electrosurgical Generator."

SUMMARY OF THE INVENTION

In a preferred embodiment, the present invention is a system for voice control of operating room electrical equipment. The system comprises an electrosurgical generator a controller with a memory, a graphical user interface controlled by said controller, a power module, a field programmable gate array, and a speech recognition module connected to said field programmable gate array, a data storage connected to said controller in said electrosurgical generator; and electrical operating room equipment connected to said speech recognition module, wherein said electrical operating room equipment is configured to receive and decrypt encrypted commands from said speech recognition module. The electrical operating room equipment may said electrosurgical generator or a robotic surgical system or other electrical equipment in an operating room. The connection between said electrical operating room equipment and said speech recognition module may be wireless. The connection between said data storage and said controller in said electrosurgical system also may be wireless.

In another preferred embodiment, the present invention is a method for voice control of electrical operating room equipment with a speech recognition system in an electrosurgical generator. The method comprises the steps of activating the speech recognition system, detecting a triggering event with the speech recognition system, identifying a voice instruction with said speech recognition system, validating grammar in an identified voice instruction, notifying the user that a voice command has been validated, encrypting the validated command, transmitting the encrypted validated command to electrical operating room equipment, receiving the encrypted validated command as the electrical operating room equipment, decrypting the received encrypted validated command at the electrical operating room equipment, determining at the electrical operating room equipment whether the decrypted command is valid, performing a safety evaluation on said decrypted command, executing the decrypted command on the electrical operating room equipment, and notifying the user that the decrypted command has been executed.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
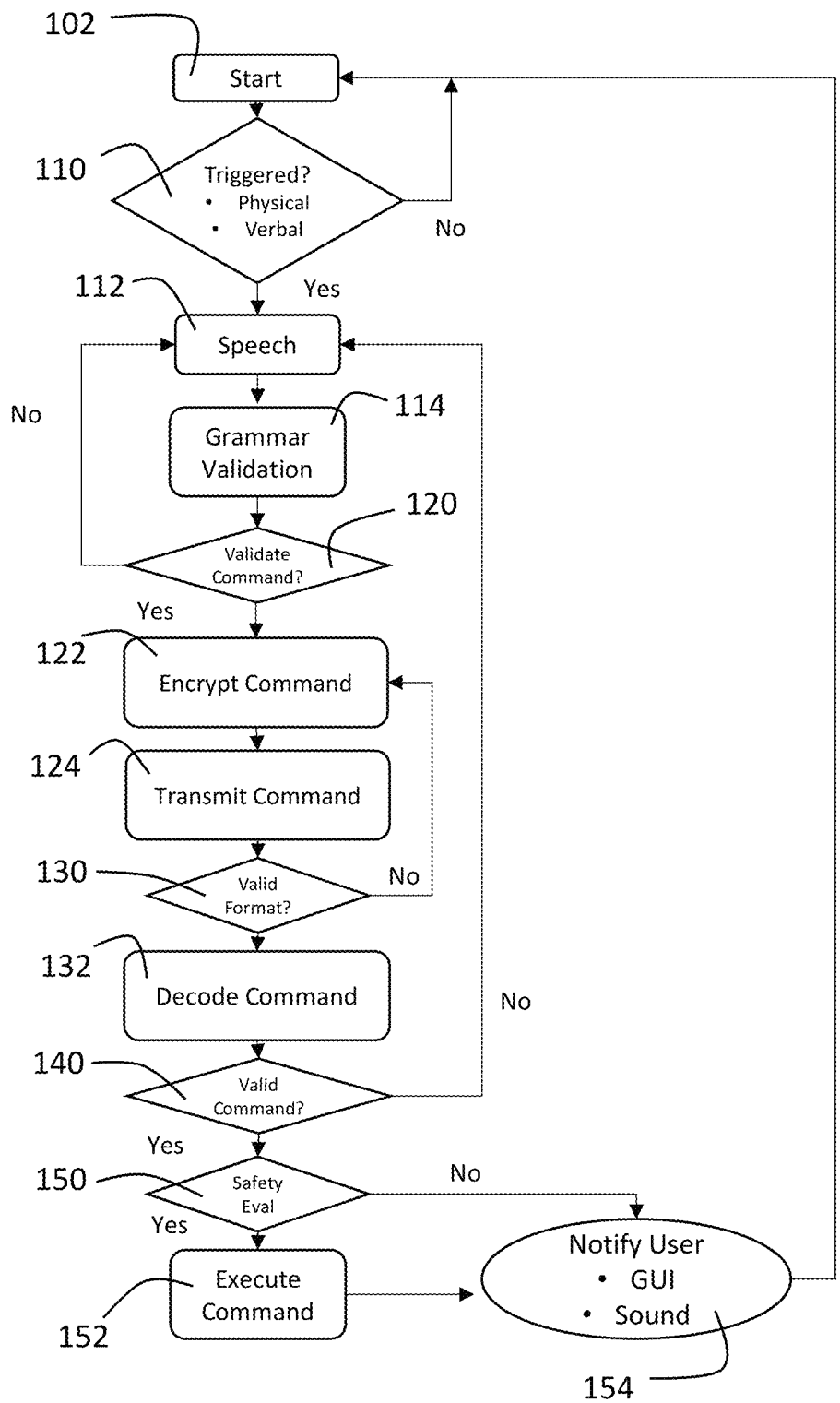
FIG. 1 is a flow chart illustrating a method for voice activation of electronic equipment in an operating room in accordance with a preferred embodiment of the present invention.

A method for voice activation of electronic equipment in an operating room in accordance with a preferred embodiment of the present invention is described with reference to FIG. 1. The method starts 102 with the voice-control system being activated or turned on. Once active or on the voice control system can be triggered 110 through physical or verbal cues or prompts. If a trigger event 110 is detected, the voice control system uses speech recognition software 112 to identify voice instructions. The grammar of the detected speech is then validated 114. If the speech is not validated as a command the system returns to the speech recognition step 112 and/or causes the system to notify the user visually or audibly that the command was not validated or returns to the detection of a new trigger 110. If a command is validated 120, the command is encrypted 122 and transmitted 124 to the electronic operating room equipment to which the command is directed.

The transmitted encrypted commend is received at the electronic equipment, which decodes the comments 132 and determines whether the decoded command is valid 130. If the decoded command is valid, the electronic equipment performs a safety evaluation 150 to ensure that the command can be safely executed. If the decoded command is deemed to be safe, the command is executed by the electronic equipment and the user is notified verbally or visually that the command has been executed. If the command is not deemed to be safe, the user is notified 154 visually or verbally.

Figure 2:
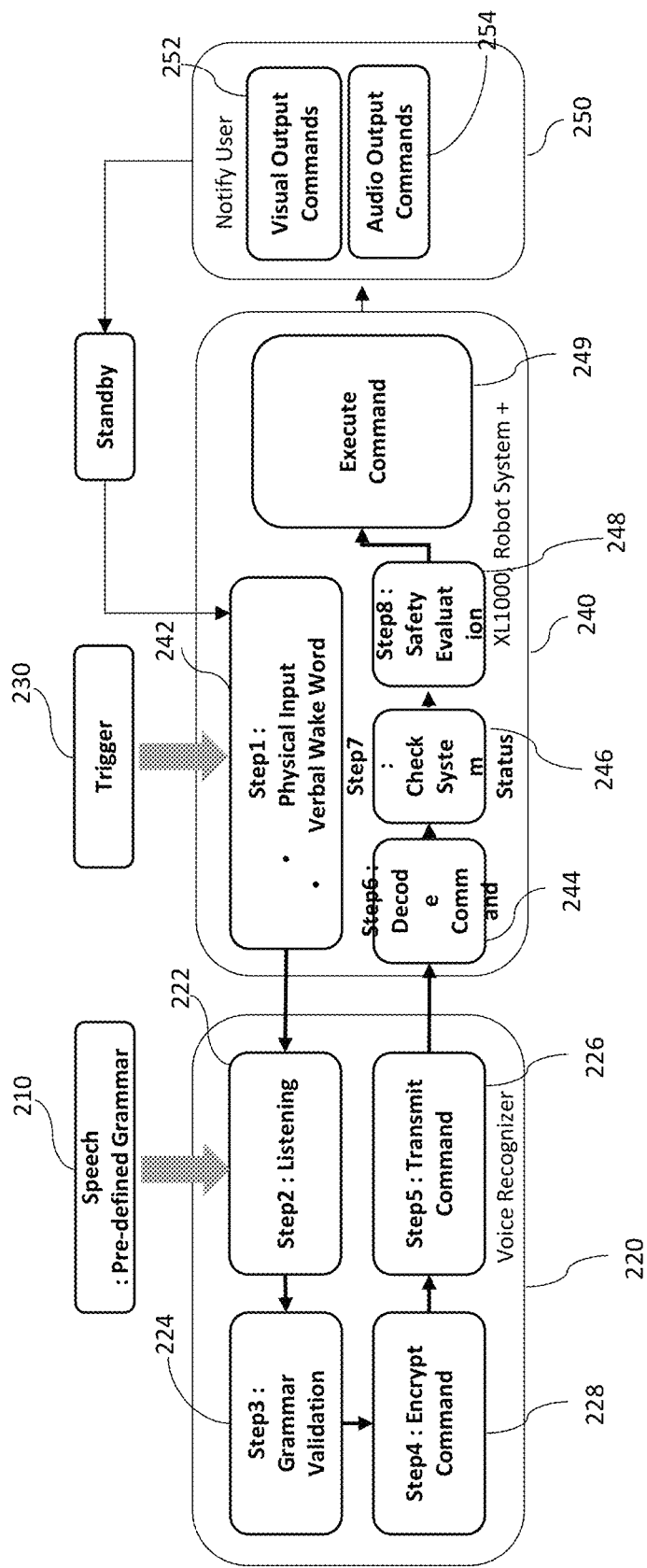
FIG. 2 is a detailed flow diagram of illustrating a method for voice activation of electronic equipment in an operating room in accordance with a preferred embodiment of the present invention.

A method for voice activation of electronic equipment in an operating room in accordance with a preferred embodiment of the present invention is further shown in the detailed flow diagram of FIG. 2. The system has pre-defined grammar (210) for speech recognition stored in memory in a processor or other memory or storage. In a preferred embodiment, the speech recognition system 220 is integrated with an electrosurgical generator so the pre-defined grammar and other speech recognition software is pre-stored in the electrosurgical generator in processor memory, other memory, or other storage in the generator. The operating room electrical equipment (240) that will be used in the procedure is triggered (230), for example, with a physical input or a wake word (242)

Once the system is activated, the speech recognition system or voice recognizer 210 listens for instructions (222). Detected speech is goes through grammar validation (224) using the pre-defined grammar (210) stored in memory or other storage. If an instruction is recognized and/or validated, the instruction or command is encrypted (226) and transmitted (228) to the equipment needed to perform the instructed task. That electronic equipment may be the electrosurgical generator, a robotic surgical system, a medical imaging system, or other operating room electrical equipment.

The transmitted encrypted command is received by the operating the operating room equipment (240) to which the instruction is directed. The operating room equipment 240 then decodes and decrypts the commend (244). The system status of the operating equipment is checked (246) and a safety evaluation is performed (248). If the commend or instruction is determined to be save the command is executed by the operating room equipment (249). The system has notification capabilities (250) to provide visual (252) or audible (254) confirmation of commands and provide other information to the user.

Figure 3:
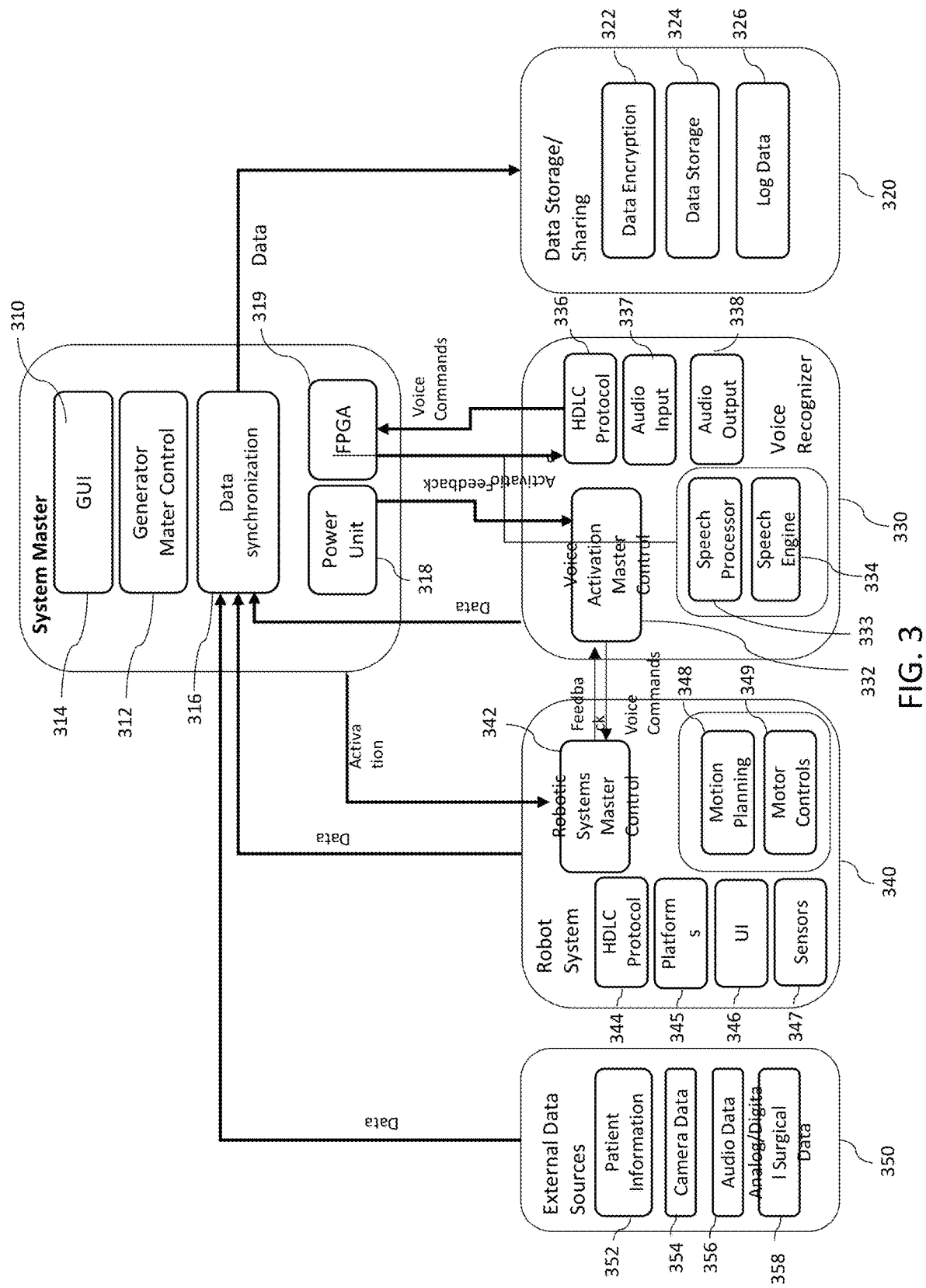
FIG. 3 is a diagram of a system for voice activation of electronic equipment in an operating room in accordance with a preferred embodiment of the present invention.

Further, a system for voice activation of electronic equipment in an operating room in accordance with a preferred embodiment of the present invention is shown in FIG. 3. In a preferred embodiment the electrosurgical generator is the master system 310. The master system 310 has a master control 312, a graphical user interface (GUI) 314, a data synchronization module 316, a power unit 318 and a field programmable gate array (FPGA) 319. The system master 310 has internally or is connected to a data storage or sharing module having data encryption 322, data storage 324 and log data 326. The system master 310 further has internally or is connected to a voice recognition system 330 having a voice activation master control 332, a speech processor 333, speech engine 334, HDLC protocol 336, audio input such as a microphone 337 and an audio input 338 such as a speaker. External equipment 240 such as a robotic surgical system is controlled with commands from the system master. The exemplary robotic surgical system has a robotic systems master control 342 that receives commands from the voice recognition system 330. The robotic system or other operating room equipment further has, for example, HDLC protocol 344, platforms 345, a user interface (UI) 346 and sensors 347. The robotic system 340 in the example further has motion panning 348 and motor controls 349. The system also may have access to external data sources 350 that may include patient information 352, camera data 354, audio data 356 and analog/digital surgical data 358.

Figure 4A:
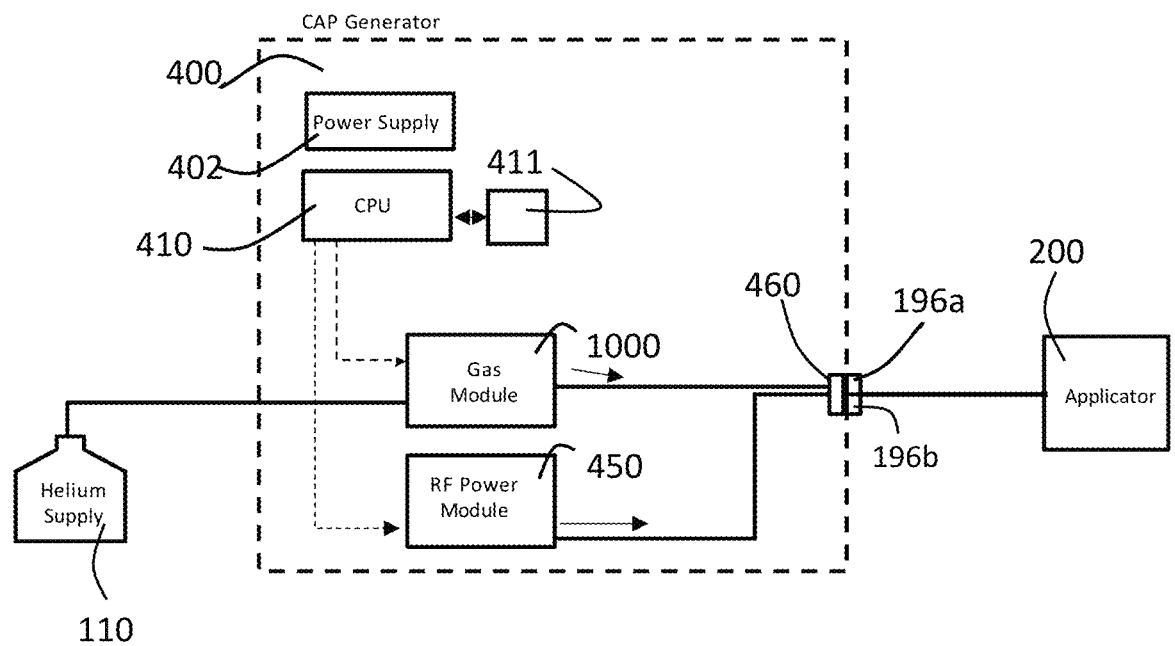
FIG. 4A is a block diagram of a cold atmospheric plasma generator of a preferred embodiment of the present invention.

The system and method of the present invention may be used with a variety of electronic equipment used in an operating room. One such system is a cold atmospheric plasma system. As shown in FIG. 4A, an exemplary cold atmospheric plasma (CAP) generator 400 has a power supply 402, a CPU (or processor or FPGA) 410 and a memory or storage 411. The system further has a display 520 (FIG. 5), which may be the display of a tablet computer. The CPU 410 controls the system and receives input from a user through a graphical user interface displayed on display 520. The CAP generator further has a gas control module 1000 connected to a source 410 of a CAP carrier gas such as helium. The CAP generator 400 further has a radio frequency (RF) power module 450 for generating radio frequency (RF) energy. The RF power module contains conventional electronics such as are known for providing RF power in electrosurgical generators. The RF Power module operates with a frequency between 10-200 kHz and output peak voltage from 3 kV to 6 kV and preferably at a frequency near (within 20%) of 40 Hz, 100 Hz or 200 Hz. The gas module 1000 and RF power module 450 are connected to connector 460 that allows for CAP joint mixer 200 (or a CAP applicator 1100 in FIGS. 11A and 11B) to be connected to the generator 400 via a connector having an electrical connector 196a and gas connector 196b.

Figure 4B:
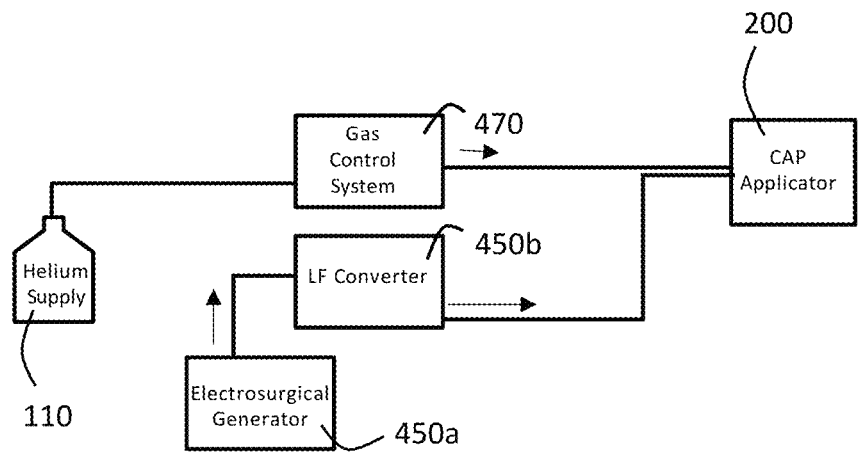
FIG. 4B is a block diagram of a plasma generator of an alternate preferred embodiment of the present invention.

As shown in FIG. 4B, other arrangements for delivery of the carrier gas and the electrical energy may be used with the invention. In FIG. 4B, a source 110 of a carrier gas (helium in this example) is provided to a gas control system 470 of any type, which supply the gas at a controlled flow rate to CAP joint mixer 200. A conventional electrosurgical generator 450a supplies high frequency (HF) energy to a low frequency converter 450b, which outputs electrical energy having a frequency in the range of 10 kHz to 200 kHz and an output voltage in the range of 3 kV to 6 Kv.

Figure 4C:
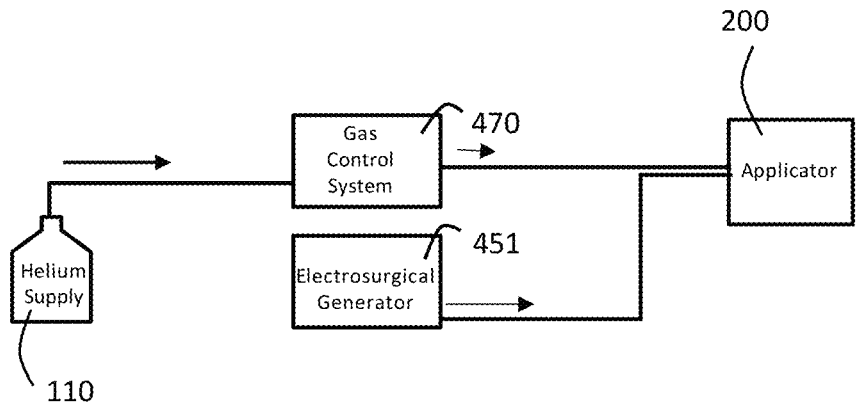
FIG. 4C is a block diagram of a plasma generator of another alternate preferred embodiment of the present invention.
Figure 4D:
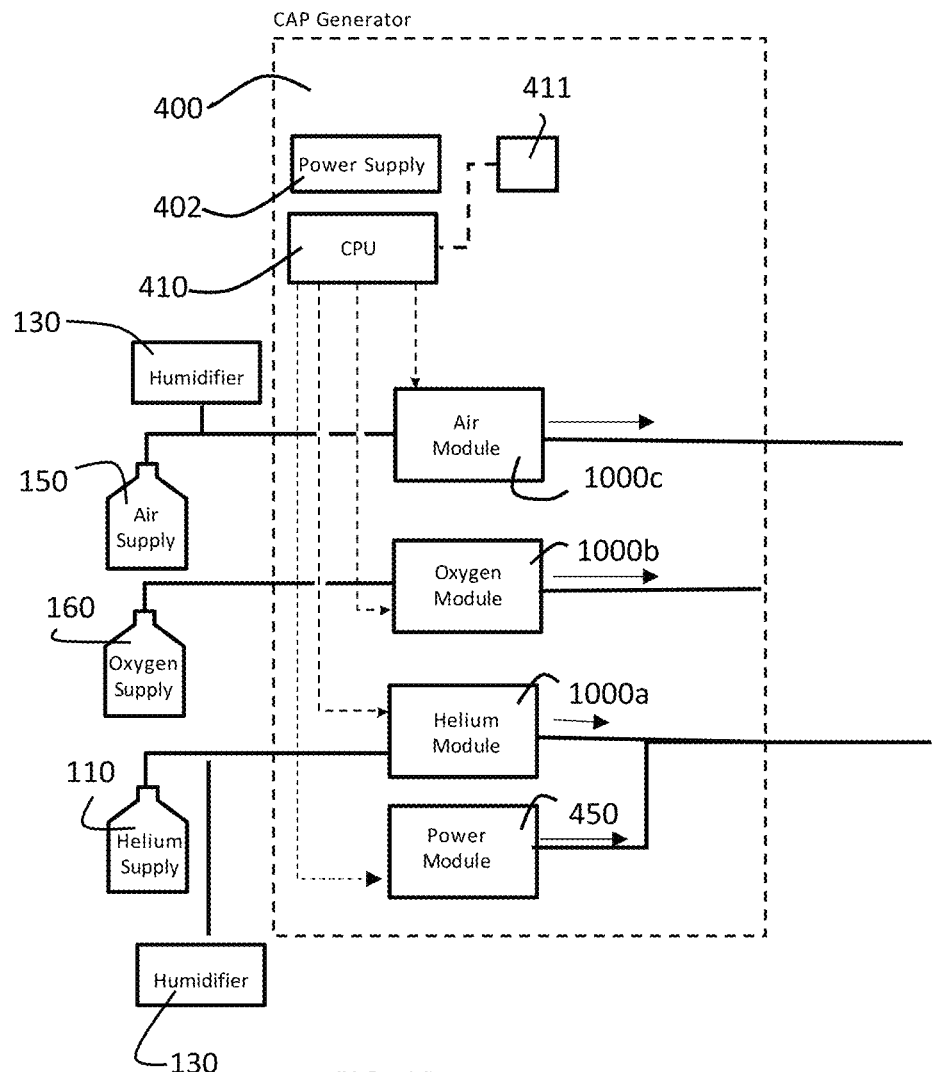
FIG. 4D is a block diagram of an integrated gas-enhanced electrosurgical generator having a plurality of gas modules of another alternate preferred embodiment of the present invention.

Another embodiment, shown in FIG. 4C, has a carrier gas source 110 connected to a conventional gas control system 470, which in turn is connected to the CAP joint mixer 200, and a conventional electrosurgical generator 451 also connected to the CAP joint mixer 200.

Figure 5:
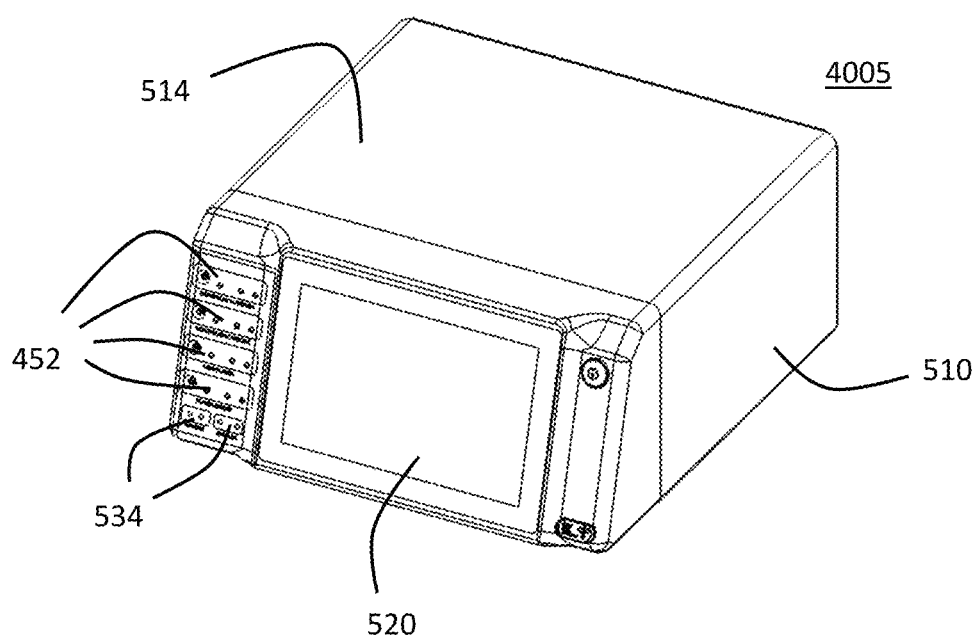
FIG. 5 is a perspective view of an integrated gas-enhanced electrosurgical generator of a preferred embodiment of the present invention.

A housing 500 for a CAP-enabled gas-enhanced electrosurgical generator 500 in accordance with a preferred embodiment of the present invention is shown in FIG. 5. The gas-enhanced generator 500 has a housing 510 made of a sturdy material such as plastic or metal similar to materials used for housings of conventional electrosurgical generators. The housing 510 has a removable cover 514. The housing 510 and cover 514 have means, such as screws, tongue and groove, or other structure for removably securing the cover to the housing. The cover 514 may comprise just the top of the housing or multiple sides, such as the top, right side, and left side, of the housing 510. The housing 510 may have a plurality of feet or legs attached to the bottom of the housing. The bottom of the housing 510 may have a plurality of vents for venting from the interior of the gas-enhanced generator.

On the face of the housing 514 there is a touchscreen display 520 and a plurality of connectors 532, 534 for connecting various accessories to the generator, such as an argon plasma probe, a hybrid plasma probe, a cold atmospheric plasma probe, or any other electrosurgical attachment. The face of the housing 510 is at an angle other than 90 degrees with respect to the top and bottom of the housing 510 to provide for easier viewing and use of the touch screen display 520 by a user. One or more of the gas control modules may be mounted within a gas-enhanced electrosurgical generator 500.

The CAP-enabled gas-assisted electrosurgical generator has a graphical user interface (GUI) for controlling the components of the system using the touch screen display 520. The graphical user interface for example, may control robotics, argon-monopolar cut/coag, hybrid plasma cut, cold atmospheric plasma, bipolar, plasma sealer, hemo dynamics or voice activation. The graphical user interface further may be used with fluorescence-guided surgery. The graphical user interface (GUI) further may be used with guided imaging such as CT, MM, or ultrasound. The graphical user interface may communicate with RFID (such as may be found in various electrosurgical attachments) and may collect and store usage data in a storage medium. The graphical user interface communicates with the field-programmable gate array ("FPGA"), which may control an irrigation pump, insufflator, full bridge for adjusting the power output, fly back for regulating the power (DC to AC) and a foot pedal. The GUI further communicates with a database of data with associated predicted CAP settings or dosages via the CPU 410. The database storage may be internal memory or other internal storage 411 or external storage.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A system for voice control of operating room electrical equipment comprising:
    an electrosurgical generator comprising:
        a controller having a memory;
        a graphical user interface controlled by said controller;
        a power module;
        a field programmable gate array; and
        a speech recognition module connected to said field programmable gate array;
    a data storage connected to said controller in said electrosurgical generator; and
    electrical operating room equipment connected to said speech recognition module, wherein said electrical operating room equipment is configured to receive and decrypt encrypted commands from said speech recognition module.

2. The system according to claim 1 wherein said electrical operating room equipment is said electrosurgical generator.

3. The system according to claim 1 wherein said electrical operating room equipment is a robotic surgical system.

4. The system according to claim 1 wherein said connection between said electrical operating room equipment and said speech recognition module is wireless.

5. The system according to claim 1 wherein said connection between said data storage and said controller in said electrosurgical system is wireless.

6. A method for voice control of electrical operating room equipment with a speech recognition system in an electrosurgical generator, the method comprising:
- activating the speech recognition system;
- detecting a triggering event with the speech recognition system;
- identifying a voice instruction with said speech recognition system;
- validating grammar in an identified voice instruction;
- notifying the user that a voice command has been validated;
- encrypting the validated command;
- transmitting the encrypted validated command to electrical operating room equipment;
- receiving the encrypted validated command as at the electrical operating room equipment;
- decrypting the received encrypted validated command at the electrical operating room equipment;
- determining at the electrical operating room equipment whether the decrypted command is valid;
- performing a safety evaluation on said decrypted command;
- executing the decrypted command on the electrical operating room equipment; and
- notifying the user that the decrypted command has been executed.

7. The method for voice control of electrical operating room equipment according to claim 6, wherein the electrical operating room equipment is the electrosurgical generator.

8. The method for voice control of electrical operating room equipment according to claim 6, wherein the electrical operating room equipment is a robotic surgical system.

* * * * *